(12) United States Patent
Fukuzawa et al.

(10) Patent No.: US 6,929,650 B2
(45) Date of Patent: Aug. 16, 2005

(54) LANCING DEVICE

(75) Inventors: Masahiro Fukuzawa, Kyoto (JP); Etsuo Hirao, Kyoto (JP)

(73) Assignee: Arkray, Inc., Kyoto (JP)

( * ) Notice: Subject to any disclaimer, the term of this patent is extended or adjusted under 35 U.S.C. 154(b) by 31 days.

(21) Appl. No.: 10/466,297

(22) PCT Filed: Jan. 10, 2002

(86) PCT No.: PCT/JP02/00106

§ 371 (c)(1),
(2), (4) Date: Jul. 11, 2003

(87) PCT Pub. No.: WO02/054952

PCT Pub. Date: Jul. 18, 2002

(65) Prior Publication Data

US 2004/0068283 A1 Apr. 8, 2004

(30) Foreign Application Priority Data

Jan. 12, 2001 (JP) .................................. 2001-004963

(51) Int. Cl.⁷ .............................................. A61B 17/32
(52) U.S. Cl. ...................... 606/182; 606/185; 606/167; 600/576
(58) Field of Search ............................... 606/181, 182, 606/185, 167, 172; 604/117, 207–211

(56) References Cited

U.S. PATENT DOCUMENTS

| 5,613,978 A | 3/1997 | Harding |
| 5,730,753 A | 3/1998 | Morita |
| 5,916,230 A | 6/1999 | Brenneman et al. |
| 5,964,718 A | 10/1999 | Duchon et al. |
| 6,156,051 A | * 12/2000 | Schraga ...................... 606/181 |

FOREIGN PATENT DOCUMENTS

| JP | 10-508527 | 8/1998 |
| JP | 11-9577 | 1/1999 |
| JP | 11-164825 | 6/1999 |
| WO | WO 97/04707 | 2/1997 |

* cited by examiner

*Primary Examiner*—Anhtuan T. Nguyen
*Assistant Examiner*—Elizabeth Houston
(74) *Attorney, Agent, or Firm*—Hamre, Schumann, Mueller & Larson, P.C.

(57) ABSTRACT

A lancing device (A) includes an auxiliary member (8) located on a side of the tip end portion of a lancet (L). By moving the auxiliary member (8), the dimension (s) of the tip end of the lancet (L) projecting from the tip end portion (8a) of the auxiliary member (8) can be varied. The variation of the dimension (S) makes it possible to stick the lancet (L) into the skin (99) of a user precisely by an intended amount.

18 Claims, 16 Drawing Sheets

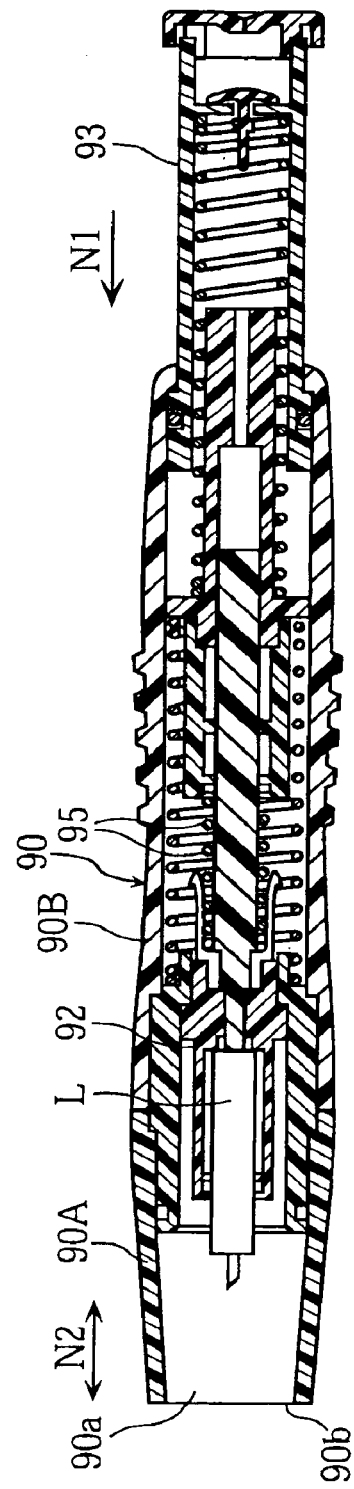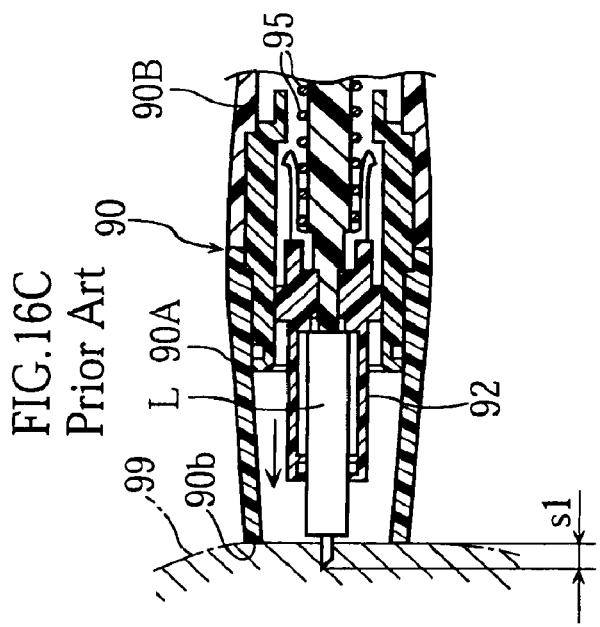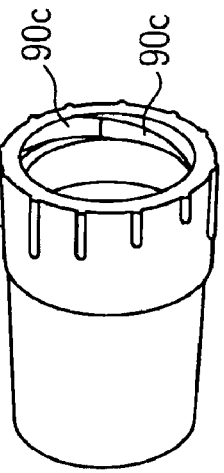

LANCING DEVICE

TECHNICAL FIELD

The present invention relates to a lancing device used for sticking a tip end of a lancet into skin for taking blood or other body fluid or tissue for examination.

BACKGROUND ART

An example of prior art lancing device is disclosed in JP-A-11-9577. As shown in FIG. 16, the prior art device includes a generally cylindrical housing 90 and a lancet holder 92 arranged in the housing for holding a lancet L. A cylindrical plunger 93 is fitted into one end of the housing 90. In this prior art device, when the plunger 93 is pushed in the arrow N1 direction, the lancet holder 92, which has latched on a predetermined portion in the housing 90, is forced to be released from the latched state. As a result, the lancet holder 92 advances toward a tip end opening 90a of the housing 90 due to the resilient force of a spring 95. As shown in FIG. 16C, a tip end surface 90b of the housing 90 is pressed against skin 99, so that the advancing movement of the lancet holder 92 causes the tip end of the lancet L to stick into the skin 99.

The housing 90 comprises two sleeves 90A and 90B connected to each other. The sleeve 90A is movable relative to the sleeve 90B in the axial direction (arrow N2 direction) of the housing 90. Specifically, as shown in FIG. 16B, the sleeve 90A has an inner circumferential surface provided with an inclined surface 90c. When the sleeve 90A is rotated, the inclined surface 90c engages with a predetermined member, which allows positional adjustment of the sleeve 90A in the arrow N2 direction.

In such a structure, as shown in FIG. 16c, by adjusting the position of the sleeve 90A, it is possible to vary the dimension s1 of the lancet L projecting from the tip end surface 90b of the housing 90 when the lancet L is advanced toward the tip end of the housing 90. Therefore, the sticking amount of the lancet L relative to the skin 99 is variable.

However, the prior art device has the following problems.

When the tip end surface 90b of the housing 90 is pressed against the skin 99 with a small force, the skin 99 is generally flush with the tip end surface. However, as shown in FIG. 17, when the pressing force relative to the skin 99 is strong, the skin 99 enters the tip end opening 90a of the housing 90. The entering amount is not constant but varies depending on the softness of the skin 99. In sticking the lancet L, negative suction pressure may often be exerted on the portion to be stuck to cause bleeding from that portion. Also in such a case, the entering amount is not constant.

However, the prior art device described above can adjust only the dimension s1 of the lancet L projecting from the tip end surface 90b of the housing 90. Therefore, the sticking amount into the skin 99 by the lancet L differs between the case where the skin 99 is flush with the tip end surface 90b as shown in FIG. 16C and the case where the skin 99 enters the tip end opening 90a as shown in FIG. 17. Further, in the case where the skin 99 enters the tip end opening 90a, the sticking amount of the lancet L varies depending on the entering amount s2. Thus, with the prior art device, sticking of the lancet L into the skin just by an intended amount is difficult. As a result, due to excess or insufficient sticking amount of the lancet L, there have been such problems that the skin is hurt more than necessary or the amount of bleeding from the portion stuck by the lancet L is insufficient.

DISCLOSURE OF THE INVENTION

An object of the present invention is to provide a lancing device which can eliminate or lessen the above-described problems.

A lancing device provided according to the present invention comprises a housing having a tip end formed with an opening, a lancet arranged in the housing, an operation mechanism for making the lancet movable to advance from within the housing toward the opening, and an auxiliary member for advancing together with the lancet toward the opening, the auxiliary member having a tip end portion located on a side of a tip end portion of the lancet, the auxiliary member being capable of varying a position relative to the lancet for varying a projecting dimension of the tip end portion of the lancet from the tip end portion of the auxiliary member.

Herein, the side of the tip end portion of the lancet means at least a part of the circumference of the tip end portion of the lancet.

In a preferred embodiment, the housing includes a sleeve rotatable relative to another portion of the housing, and the variation of the position of the auxiliary member relative to the lancet is performed by rotating the sleeve.

In a preferred embodiment, the lancing device includes a cam mechanism which moves the auxiliary member in a back-and-forth direction of the lancet when the auxiliary member is rotated relative to the lancet, and the auxiliary member engages the sleeve to rotate relative to the lancet by rotating the sleeve.

In a preferred embodiment, the device further comprises a lancet holder for removably holding the lancet, and the advancing movement of the lancet is performed by moving the lancet holder by an operation of the operation mechanism.

In a preferred embodiment, the auxiliary member is attached to the lancet holder.

In a preferred embodiment, the auxiliary member and the lancet holder are attached together by threading engagement, and the variation of the position of the auxiliary member relative to the lancet is performed by rotating the auxiliary member and the lancet holder relative to each other.

In a preferred embodiment, the tip end portion of the auxiliary member surrounds an entire circumference of the tip end portion of the lancet.

In a preferred embodiment, the lancet includes a main body and a needle projecting from a tip end surface of the main body, and the tip end portion of the auxiliary member is provided with a patch plate portion facing the tip end surface of the main body. The patch plate portion is formed with a hole for passing the needle.

In a preferred embodiment, the auxiliary member has a configuration capable of allowing the needle of the lancet to project from the tip end portion of the auxiliary member entirely throughout the length.

In a preferred embodiment, the operation mechanism comprises a resilient member for biasing the lancet holder in the housing toward the opening, a latch member for latching the lancet holder in the housing against resilient force of the resilient member, an operation member exposed to an outside of the housing at least partially, and a latch release member which operates to release the lancet holder from the latched state when the operation member is operated.

In a preferred embodiment, the device further comprises a pump mechanism. The pump mechanism comprises a cylinder and a plunger defining a pressure chamber capable of communicating with an outside of the housing through an exhaust vent and capable of communicating with an inside of the tip end portion of the housing through an intake vent, a plunger operation mechanism for reciprocally moving the plunger relative to the cylinder by an operation different from the operation of the operation mechanism, a first non-return valve for opening or closing the exhaust vent, the first non-return valve keeping the exhaust vent open when the plunger reduces a volume of the pressure chamber, and a second non-return valve for opening or closing the intake vent, the second non-return valve keeping the intake vent open when the plunger increases the volume of the pressure chamber.

In a preferred embodiment, the plunger operation mechanism comprises an outer cylinder arranged outwardly on the housing for reciprocal movement, and connecting means for connecting the plunger to the outer cylinder so that the plunger moves reciprocally relative to the cylinder when the outer cylinder moves reciprocally.

Other features and advantages of the present invention will become clearer from the description of the embodiments of the present invention given below.

BRIEF DESCRIPTION OF THE DRAWINGS

FIG. 16A is a sectional view illustrating an example of prior art device, FIG. 16B is a perspective view of a part of the prior art device, and FIG. 16C is a sectional view of a principal portion of the prior art device for illustrating the operation.

BEST MODE FOR CARRYING OUT THE INVENTION

Preferred embodiments of the present invention will be described below in detail with reference to the accompanying drawings.

Figure 1:
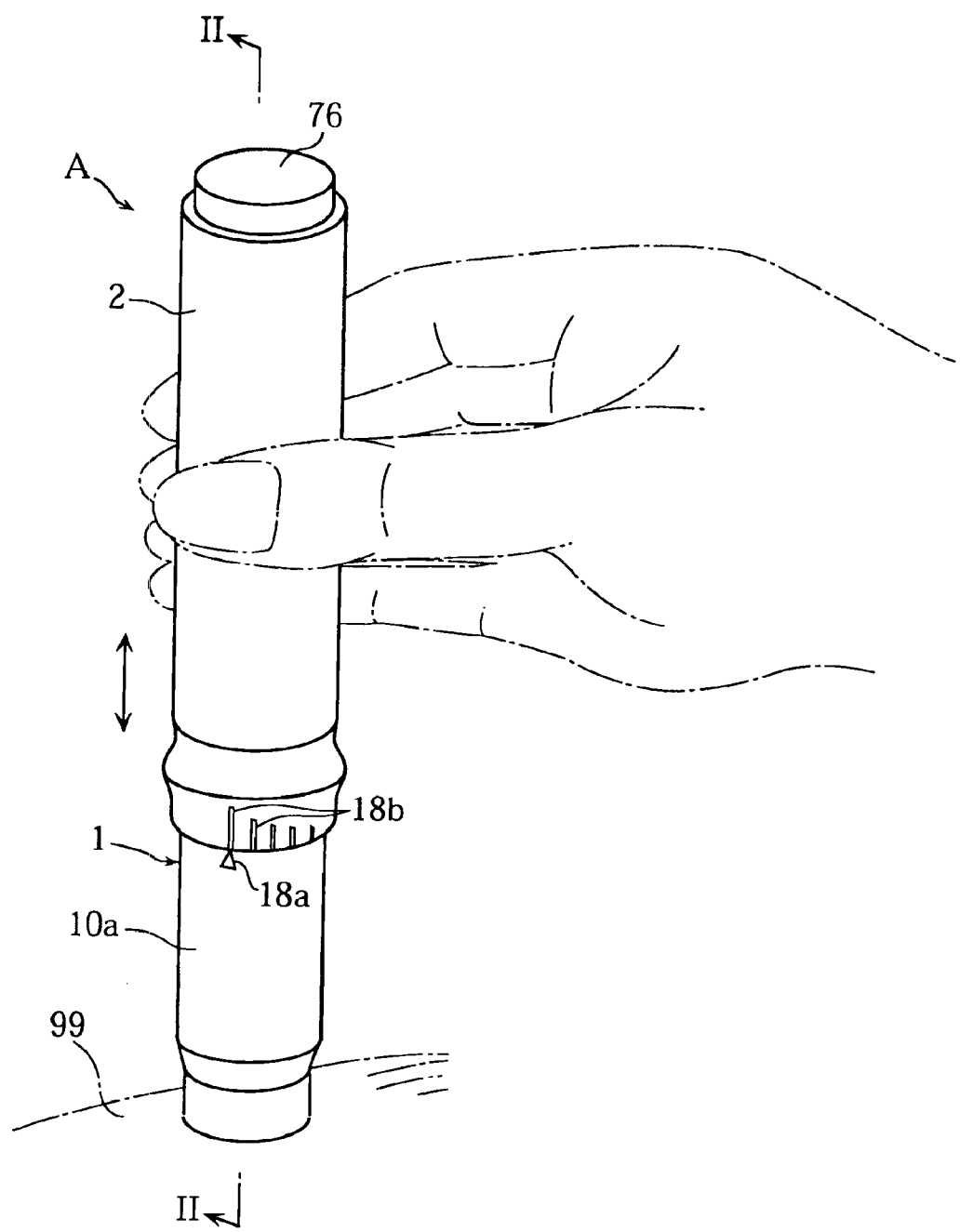
FIG. 1 is a perspective view illustrating an example of lancing device according to the present invention.
Figure 2:
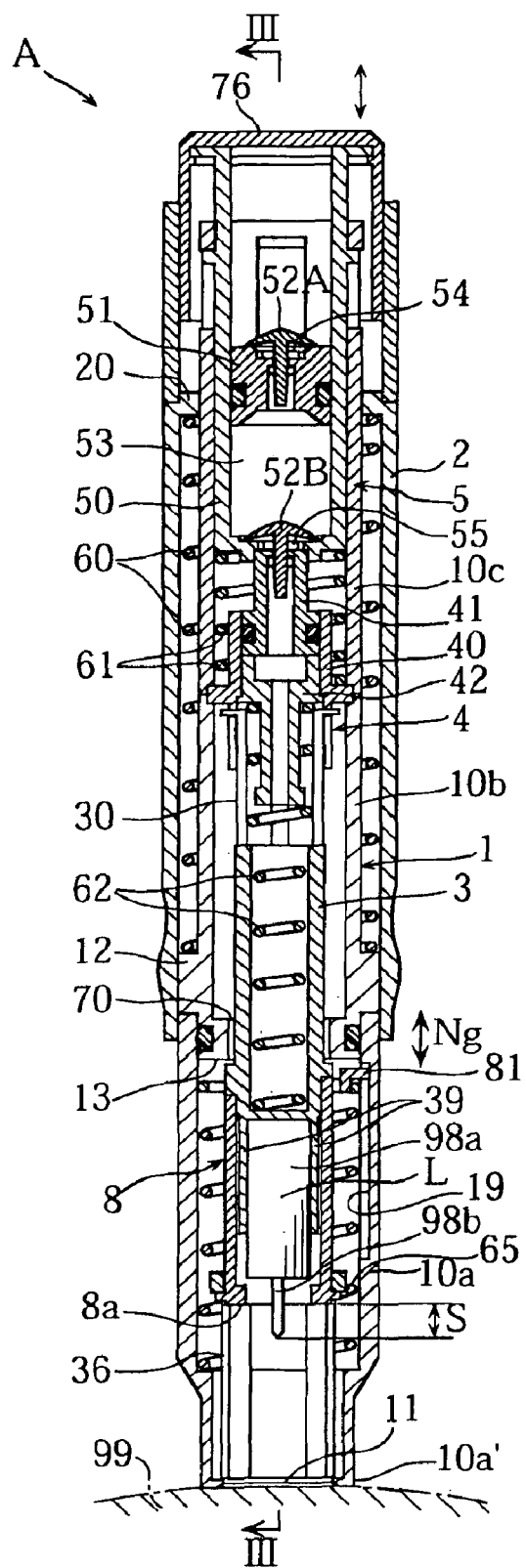
FIG. 2 is a sectional view taken along lines II—II in FIG. 1.

FIGS. 1–11 illustrate an example of a lancing device according to the present invention. As shown in FIG. 2, the lancing device A in this embodiment includes a housing 1, an outer cylinder 2, a lancet holder 3 for removably holding a lancet L, an auxiliary member 8 attached to the lancet holder 3, a latch mechanism 4 for the lancet holder 3, and a pump mechanism 5 defining a pressure chamber 53 for producing negative pressure. The lancet L comprises a generally columnar main body 98a formed of e.g. synthetic resin and a metal needle 98b projecting from the tip end surface of the main body. Preferably, for good hygiene, the lancet L is used only once and disposed after use.

The housing 1 comprises, for example, three sleeves 10a–10c connected to each other in series and has a generally cylindrical configuration having a tip end formed with an opening 11. The sleeve 10a constitutes a portion of the housing 1 adjacent to the tip end and is rotatable relative to the sleeve 10b. The sleeve 10a has a tip end 10a' to be pressed against a user's skin and is removable from the sleeve 10b. Such removable arrangement of the sleeve 10a makes it possible to replace the sleeve 10a with a new one when sampled body fluid accidentally adheres to this sleeve.

The lancet holder 3 has a tip end portion provided with a generally cylindrical holding piece 39 for holding the main body 98a of the lancet L fitted therein. The lancet holder 3 is reciprocally movable in the axial direction Ng of the housing 1 (corresponding to the back-and-forth direction of the lancet L) and can be latched on a predetermined position in the housing 1 by the latch mechanism 4. The lancet holder 3 can move forward toward the opening 11 when it is released from the latched state. The structure will later be described in detail.

The auxiliary member 8, which is generally cylindrical, is rotatably arranged outwardly on the tip end portion of the lancet holder 3 to surround the outer circumference of the lancet L almost throughout its length while being slidably fitted to a generally cylindrical guide member 36 provided in the tip end portion of the housing 1. The auxiliary member 8 has a tip end portion 8a, which engages with the user's skin 99 in sticking the lancet L into the skin 99 and which has an outer diameter smaller than the inner diameter of the opening 11 of the tip end of the housing 1. In detaching the sleeve 10a from the sleeve 10b, the sleeve 10a holds the auxiliary member 8 together with the guide member 36 so as not to hinder the attaching or detaching of the lancet L relative to the lancet holder 3. When at least portions adjacent to the tip end of the guide member 36 and the sleeve 10a are made transparent, bleeding from the portion where the lancet L is stuck can be checked visually. The present invention may employ such a structure.

The auxiliary member 8 is upwardly provided with an engagement projection 81 engaging with a groove 19 formed at an inner wall surface of the sleeve 10a. Therefore, as clearly shown in FIG. 4, when the sleeve 10a is rotated in the arrow Nh direction, the auxiliary member 8 rotates together with the sleeve in the same direction. The auxiliary member 8 and the lancet holder 3 constitute a cam mechanism C. The cam mechanism C comprises a cam surface 89 formed at the upper end of the auxiliary member 8 and including a surface inclined relative to the axial direction NG of the housing 1, and a projection 38 formed at an outer surface of the lancet holder 3 for engagement with the cam surface 89. In the cam mechanism C, when the auxiliary member 8 is rotated in the arrow Nh direction, the engaging position of the projection 38 relative to the cam surface 89 deviates to move the auxiliary member 8 in the axial direction Ng of the housing 1. The groove 19 extends in the axial direction Ng of the housing 1 for allowing the movement of the auxiliary member 8 in that direction. The tip end portion of the housing 1 is inwardly provided with a spring 65 for pushing the auxiliary member 8 toward a head of the housing 1 with a relatively small force so as not hinder the advancing movement of the lancet holder 3 (See FIG. 2). The resilient force of the spring 65 keeps the engagement between the cam surface 89 and the projection 38 so that the auxiliary member 8 is reciprocally movable in the axial direction Ng of the housing 1 in accordance with the movement of the lancet holder 3.

Figure 3:
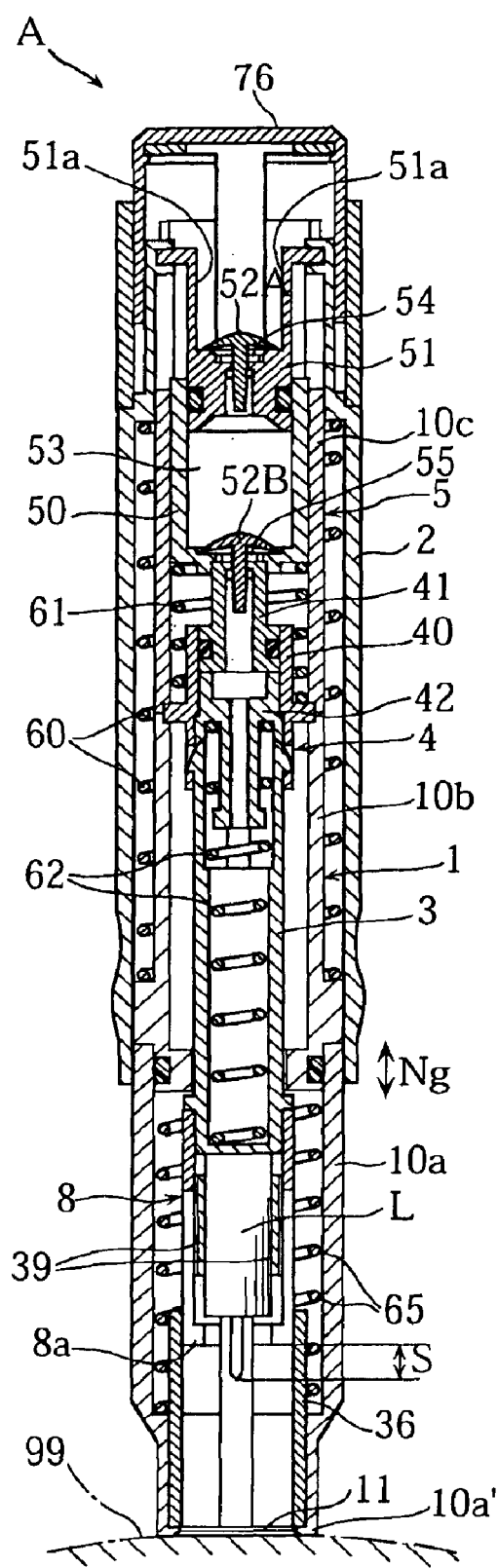
FIG. 3 is a sectional view taken along lines III—III in FIG. 2.
Figure 4:
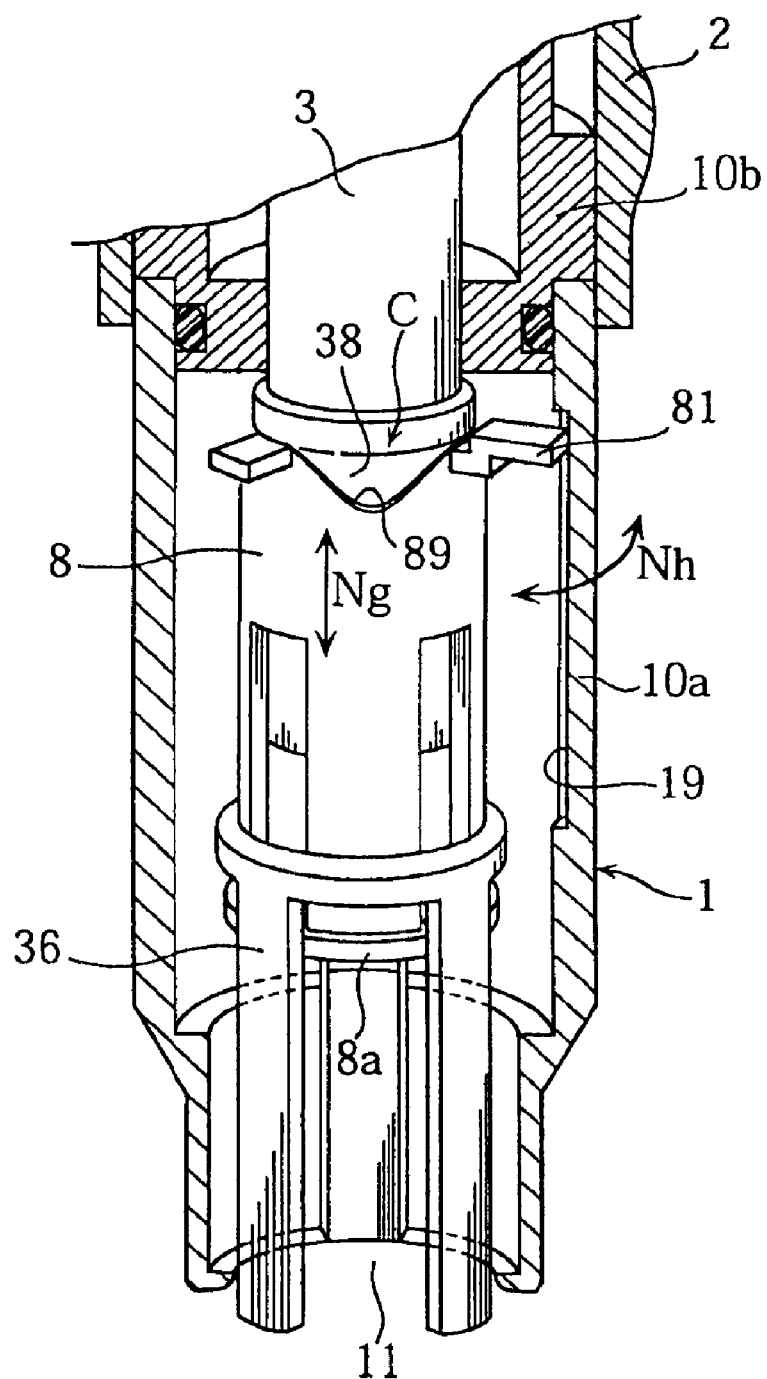
FIG. 4 is an enlarged perspective view, partially in section, illustrating a principal portion of the lancing device of FIG. 1.

In the lancing device A, since the auxiliary member 8 is movable relative to the lancet holder 3 in the axial direction Ng of the housing 1, the tip end portion of the lancet L can be caused to project downward from the tip end portion 8a of the auxiliary member 8 as clearly shown in FIGS. 2 and 3, and the projecting amount S can be adjusted. As clearly shown in FIG. 1, outer circumferential surfaces of the sleeves 10a and outer cylinder 2 are formed with a reference line 18a and a plurality of scales 18b, respectively, as marks for adjusting the projecting amount S.

Figure 12:
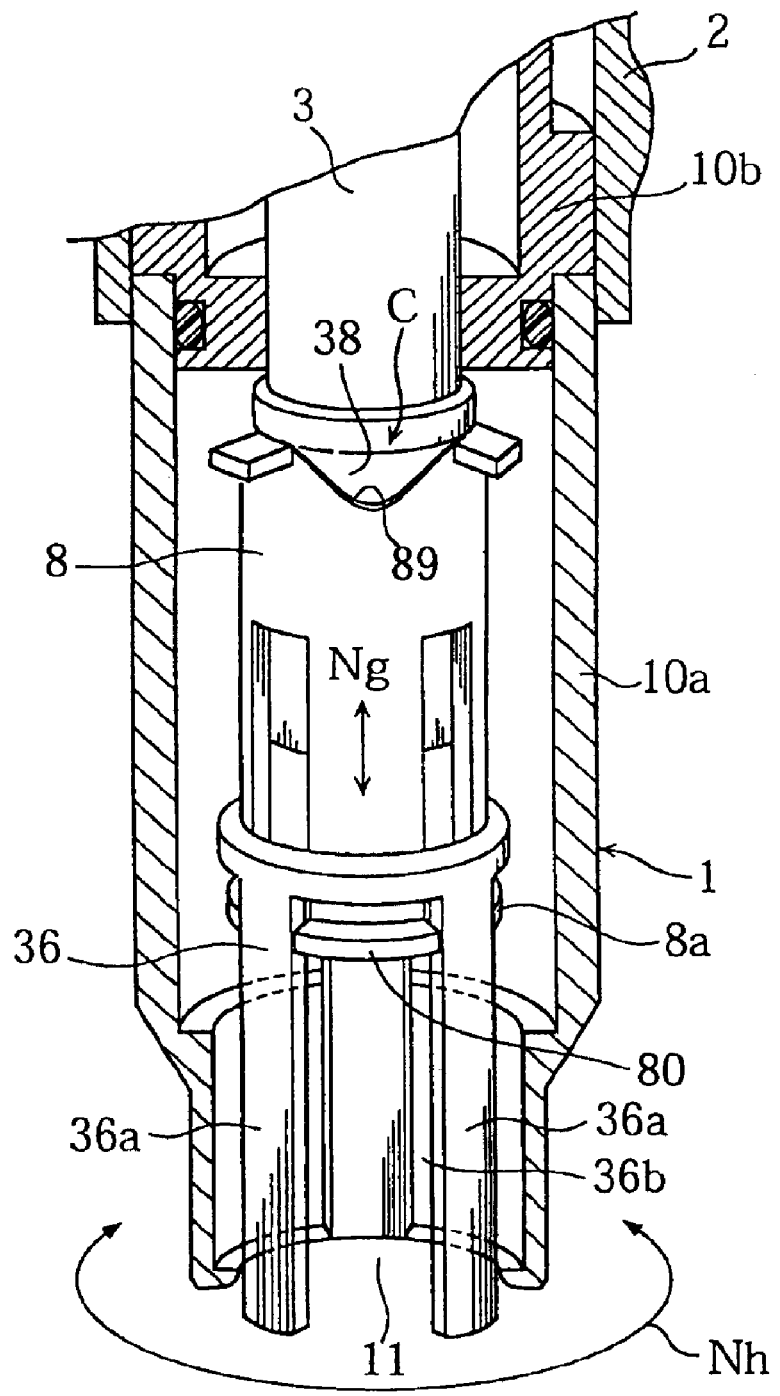
FIG. 12 is a perspective view, partially in section, illustrating a principal portion of another embodiment of the present invention.

In the present invention, a mechanism as shown in FIG. 12 may be used instead of the above-described mechanism for making the auxiliary member 8 rotate together with the rotation of the sleeve 10a. In the mechanism shown in the figure, the tip end portion 8a of the auxiliary member 8 has an outer circumference surface formed with a projection 80. The projection 80 is fitted in a slit 36b defined between a pair of plate portions 36a of the guide member 36, thereby engaging each of the plate portions 36a. With this structure, when the sleeve 10a and the guide member 36 are rotated in the arrow Nh direction by operating the sleeve 10a, the auxiliary member 8 also rotates together with these members. Therefore, by the operation of the cam mechanism C, the auxiliary member 8 moves relative to the lancet holder 3 in the axial direction Ng of the housing 1. The projection 80 of the auxiliary member 8 is movable in the slit 36b in the axial direction Ng of the guide member 36 for allowing proper movement of the auxiliary member 8 in the axial direction of the housing 1. When this structure is utilized, unlike the structure shown in FIG. 4, it is not necessary to form the groove 19 at the inner wall of the sleeve 10a, which simplifies the structure of the apparatus.

As clearly shown in FIG. 2, the outer cylinder 2 is arranged outwardly on the housing 1 for reciprocal sliding movement in the axial direction Ng. After the outer cylinder 2 is pushed downward relative to the housing 1, the outer cylinder 2 returns to its original position due to the resilient force of a spring 60. Specifically, an inner circumferential surface of the outer cylinder 2 at the upper portion and an outer circumferential surface of the housing 1 at the axially intermediate portion are provided with stepped portions 20 and 12, respectively, which define a gap between the outer cylinder 2 and the housing 1. The spring 60 is arranged in this gap. The spring 60, which is a coil compression spring, functions to return not only the outer cylinder but also a plunger 51 upward, which will be described later.

The pump mechanism 5 comprises a cylinder 50, the plunger 51 and a first and a second non-return valves 52A, 52B. The cylinder 50 and the plunger 51 define the pressure chamber 53. The cylinder 50 is fitted in an upper portion of the housing 1 for reciprocal movement within a predetermined stroke. The cylinder 50 and the plunger 51 define the pressure chamber 53. The cylinder 50 is fitted in an upper portion of the housing 1 for reciprocal movement within a predetermined stroke. The cylinder 50 has an upper portion to which a head cap 76 for pushing operation is attached to project higher than the upper end of the outer cylinder 2. When the head cap 76 is pushed down, the cylinder 50 also moves downward. The head cap 76 is an example of operation member in the present invention. A spring 61 is arranged below the cylinder 50 so that the cylinder 50 after pushed down can return to its original position due to the resilient force of the spring 61. The spring 61 is supported by a sleeve 40, which will be described later.

The plunger 51 is fitted in the cylinder 50 for reciprocal sliding movement. As clearly shown in FIG. 3, the plunger 51 is provided with a pair of arms 51a, which are connected to an upper portion of the outer cylinder 2. Therefore, when the outer cylinder 2 moves reciprocally in the axial direction Ng of the housing 1, the plunger 51 correspondingly moves reciprocally in the cylinder 50. In this embodiment, the outer cylinder 2 constitutes a plunger operation mechanism in the present invention. The cylinder 50 is provided with cutouts for avoiding its interference with the arms 51a.

The plunger 51 is provided with an exhaust vent 54 for discharging air existing in the pressure chamber 53 to the outside of the housing 1. The first non-return valve 52A, which is attached to the plunger 51, is provided with a flexible collar for opening or closing the exhaust vent 54. The first non-return valve 52A allows air flow from within the pressure chamber 53 to the outside of the housing 1, but blocks air flow into the pressure chamber 53 from the outside.

The cylinder 50 has a bottom portion provided with an intake vent 55 for causing air existing in the housing 1 to flow into the pressure chamber 53. A continuous communication path is formed in the housing 1 for providing communication between the intake vent 55 and the interior of the tip end portion of the housing 1. Specifically, as clearly shown in FIG. 2, the intake vent 55 communicates with the interior of the tip end portion of the housing 1 via through-holes provided respectively at a first and a second push members 41 and 42 which will be described later, a plurality of slits 30 provided at an upper portion of the lancet holder 3, and a gap 70 defined between a stepped portion 13 of the housing 1 and the lancet holder 3.

The second non-return valve 52B, which serves to open or close the intake vent 55, is also provided with a flexible collar similarly to the first non-return valve 52A. The second non-return valve 52B allows air flow from the outside of the pressure chamber 53 into the pressure chamber 53, but blocks air flow from the inside of the pressure chamber 53 to the outside.

Figure 5:
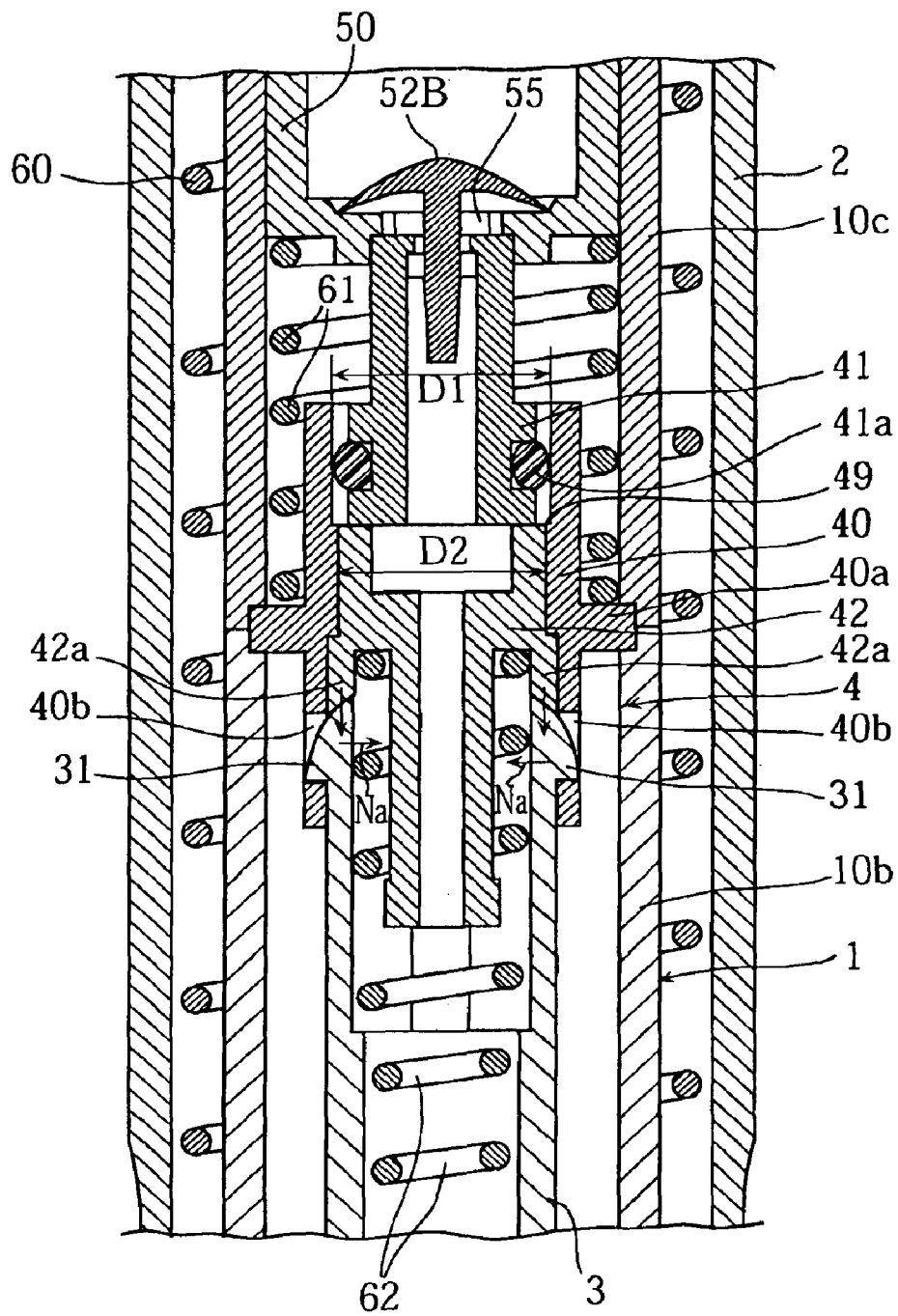
FIG. 5 is an enlarged sectional view illustrating a principal portion of FIG. 3.
Figure 6:
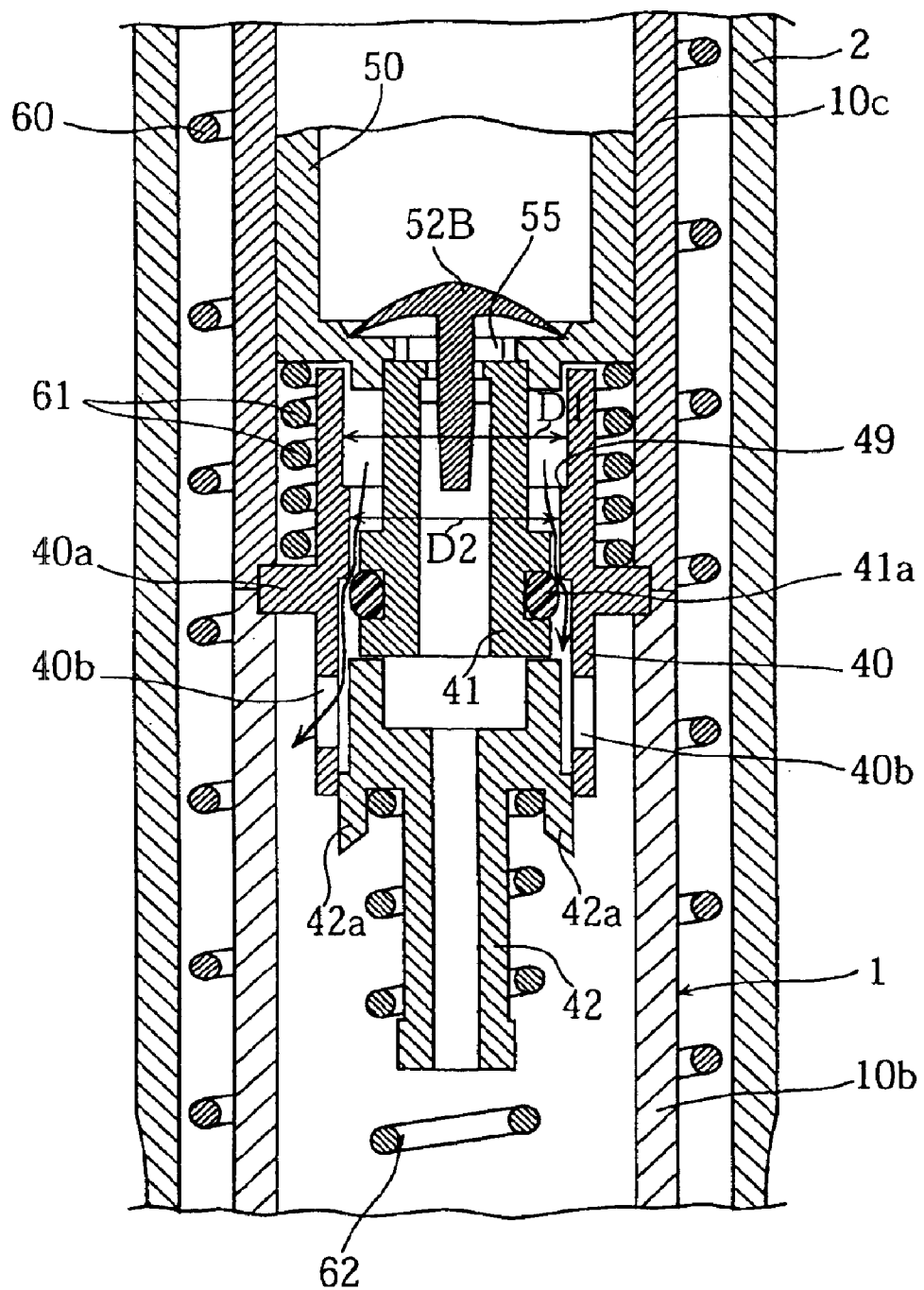
FIG. 6 illustrates the operation of the portion shown in FIG. 5.

As clearly shown in FIG. 5, the latch mechanism 4 comprises the sleeve 40 and the first and the second push members 41, 42 reciprocally fitted in the sleeve 40. The sleeve 40, which is an example of latch member in the present invention, has a flange 40a sandwiched between the two sleeves 10b and 10c of the housing 1, thereby being fixed in the housing 1 below the cylinder 50. The sleeve 40 has a lower portion formed with a pair of holes 40b for engagement with a pair of latch engagement pawls 31 formed at an upper end portion of the lancet holder 3. The upper portion of the lancet holder 3 is provided with a spring 62 as a coil pressure spring having an upper end engaging the second push member 42. The lancet holder 3 can latch on the sleeve 40 by the engagement of each engagement pawl 31 with the relevant hole 40b with the spring 62 compressed. The latching can be performed by manually pushing the lancet holder 3 upwardly in the housing 1 after the lancet L is attached to the lancet holder.

The first push member 41 is connected to the bottom portion of the cylinder 50 for reciprocal movement together with the cylinder 50. The first push member 41 has a lower portion fitted in the sleeve 40. The second push member 42 has an upper portion fitted in the sleeve 40 for reciprocal movement therein and engaging the bottom surface of the first push member 41 due to the resilient force of the spring 62. The second push member 42, which is an example of latch release member in the present invention, has a pair of projections 42a respectively located above the engagement pawls 31 of the lancet holder 3. Each of the projections 42a and each of the engagement pawls 31 are provided with predetermined tapered surfaces corresponding to each other. Thus, when the projections 42a are moved downward to a position lower than the state shown in FIG. 5, the projections 42a push the respective engagement pawls 31 for deformation toward the center of the housing 1, i.e. in the direction indicated by the arrow Na. As a result, the engagement pawls 31 are disengaged from the sleeve 40.

The first push member 41 is provided with an O-ring 41a formed of rubber for achieving airtightness between the first push member 41 and the inner circumferential surface of the sleeve 40. The inner circumferential surface of the sleeve 40 is provided with a stepped portion 49 so that, in moving the push member 41 downward by pushing the head cap 76, the resistance relative to the pushing operation varies. Specifically, the inner diameter D1 at an upper portion of the sleeve 40 is slightly larger than the inner diameter D2 at a lower portion of the sleeve. It is set so that, in the case where the O-ring 41a moves downward together with the first push member 41, the O-ring 41a just comes to the stepped portion 49 when the second push member 42 disengages the engagement pawls 31 from the sleeve 40. As clearly shown in FIG. 6, the first push member 41 can move downward until the O-ring 41a finishes passing the portion having the inner diameter D2, but in such a state, the portion where the first push member 41 and the sleeve 40 fit to each other is released from the airtight state.

Next, the usage and operation of the lancing device A will be described.

As shown in FIGS. 2 and 3, for using the lancing device A, a lancet holder 3 holding a lancet L is first latched on the sleeve 40. Subsequently, as shown in FIG. 1, with the tip end of the housing 1 brought in contact with a user's skin 99, the outer cylinder 2 is moved reciprocally upward and downward. This operation can be performed easily, because the outer cylinder 2 is easy to hold and the outer cylinder 2 moves upward due to the resilient force of the spring 60.

Figure 7A:
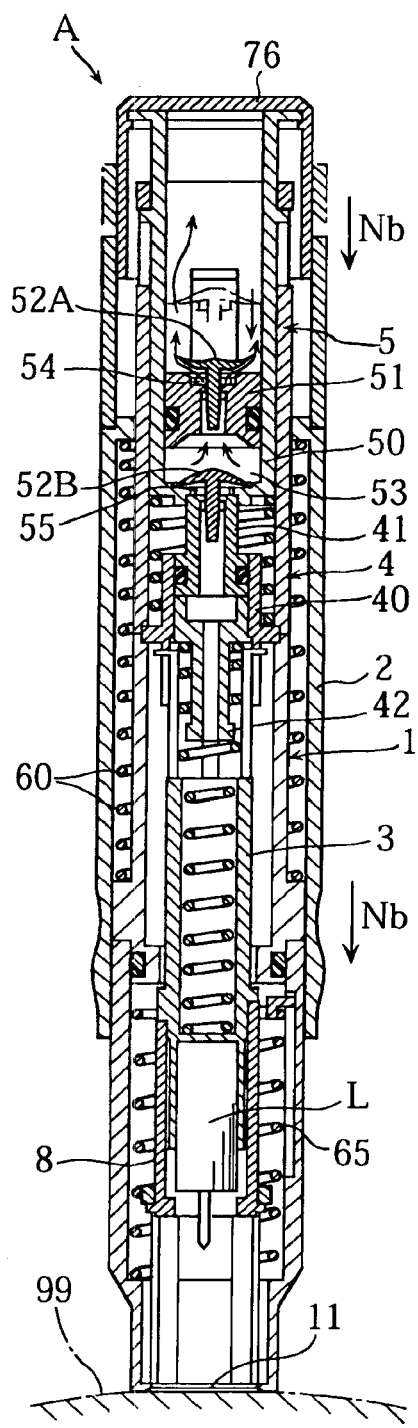
FIGS. 7A and 7B are sectional views illustrating the operation in producing negative pressure.
Figure 7B:
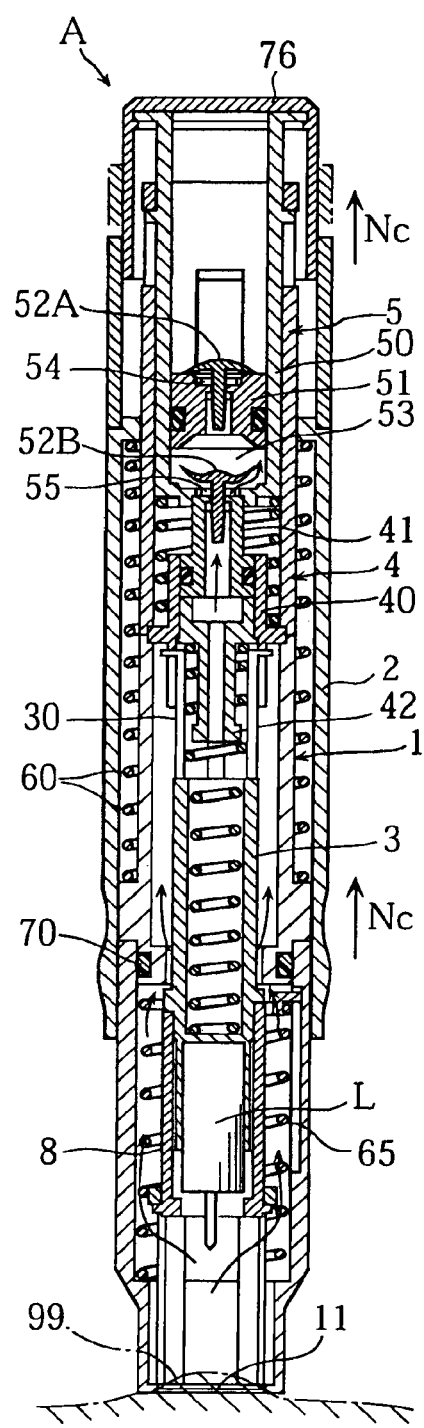
Figure 8:
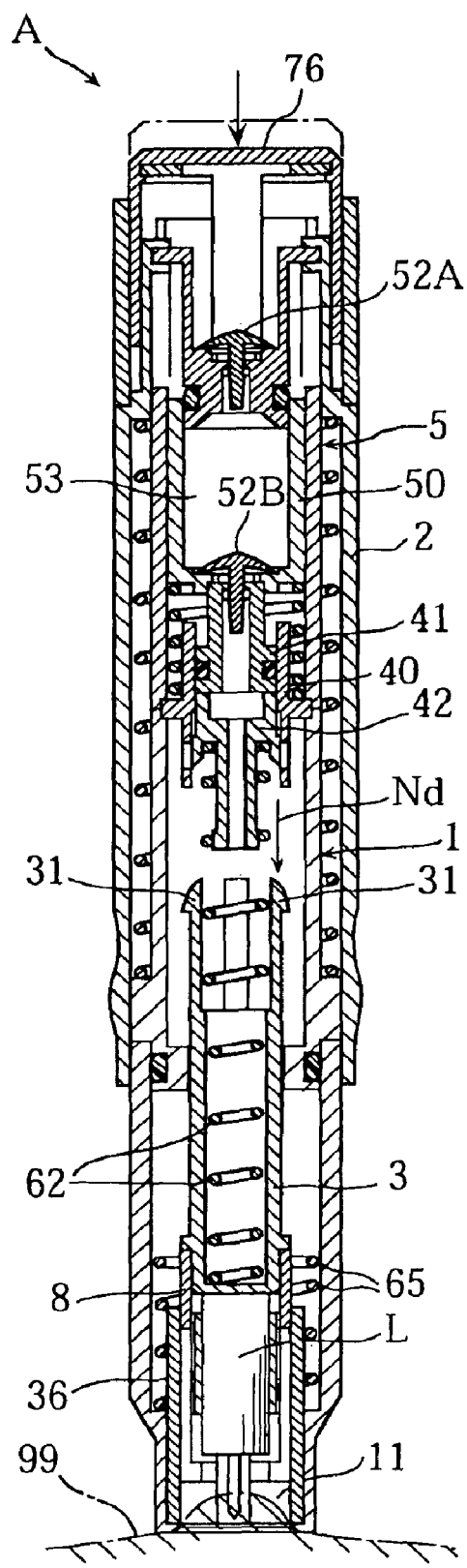
FIG. 8 is a sectional view illustrating the advancing movement of the lancet.

As clearly shown in FIG. 7A, when the outer cylinder 2 moves downward in the arrow Nb direction, the plunger 51 also moves downward. At that time, the second non-return valve 52B is closed, whereas the first non-return valve 52A is open, so that air in the pressure chamber 53 is discharged to the outside of the housing 1 through the exhaust vent 54. As shown in FIG. 7B, when the outer cylinder 2 then moves upward in the arrow Nc direction, the plunger 51 also moves upward. As a result, the volume of the pressure chamber 53 increases to produce negative pressure in the pressure chamber 53. At that time, the first non-return valve 52A is closed, whereas the second non-return valve 52 is open. Therefore, negative pressure is also produced in the tip end portion of the housing 1, and the negative pressure acts on the skin 99.

In the case where the outer cylinder 2 is further moved reciprocally following the above-described operation, negative pressure in the tip end portion of the housing 1 is properly maintained because the second non-return valve 52B is closed when the plunger 51 moves downward. Therefore, as the reciprocal movement of the outer cylinder 2 is repeated, negative pressure in the pressure chamber 53 and in the tip end portion of the housing 1 is gradually increased (the absolute pressure is decreased). Thus, in the lancing device A, the negative pressure to be exerted on the skin 99 can be appropriately controlled by increasing or decreasing the number of times of the reciprocal movement of the outer cylinder 2.

Subsequently, to stick the lancet L into the skin 99, the head cap 76 is depressed with fingers. This operation causes the cylinder 50 and the first and the second push member 41, 42 to move downward. The second push member 42 pushes each engagement pawl 31 of the lancet holder 3 so that the lancet holder 3 is released from its latched state on the sleeve 40. As a result, as clearly shown in FIG. 8, the lancet holder 3 advances quickly in the arrow Nd direction toward the opening 11 at the tip end of the housing 1, and the tip end portion of the lancet L sticks into the skin 99. When the head cap 76 is further depressed from this state, the O-ring 41a of the first push member 41 shown in FIG. 5 moves from the portion with the inner diameter D1 to the portion with the inner diameter D2 of the sleeve 40. Therefore, the resistance to the pushing operation of the head cap 76 increases, which duly notifies the user that the advancing movement of the lancet L described above is completed.

Figure 9:
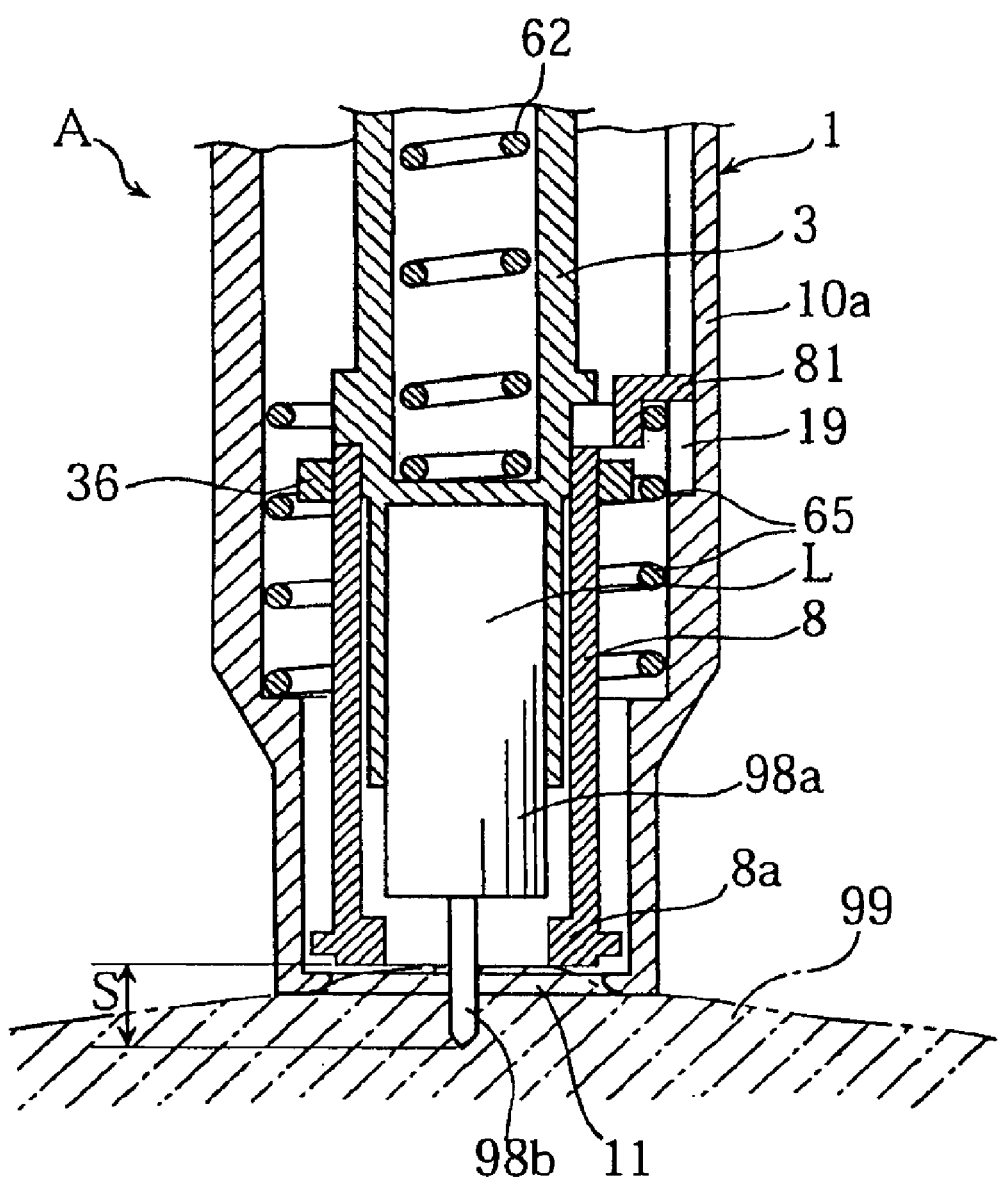
FIG. 9 is a sectional view illustrating a principal portion in a state where the lancet is stuck into the skin.

As clearly shown in FIG. 9, when the tip end portion of the lancet L sticks into the skin 99, the tip end portion 8a of the auxiliary member 8 comes into contact with the skin 99. Thus, the auxiliary member 8 serves as a stopper to prevent the lancet holder 3 and the lancet L from advancing over a predetermined distance. Therefore, among the tip end portion of the lancet L, only a portion (having a dimension S) projecting downward from the tip end portion 8a of the auxiliary member 8 sticks into the skin 99. The sticking amount is generally equal to the dimension S regardless of the dimension of the skin entering the opening 11 at the tip end of the housing 1 due to negative pressure. The sticking amount can be made much closer to the above-described dimension S by making the diameter of the opening at the tip end portion of the auxiliary member 8 smaller and hence closer to the diameter of the needle 98b.

The dimension S described above can easily be varied by rotating the sleeve 10a. Therefore, the sticking amount of the lancet L into the skin 99 can appropriately be varied depending on such conditions that the portion to be stuck with the lancet L is likely to bleed or not. Thus, it is possible to eliminate such problems that the skin 99 is hurt more than necessary or bleeding is difficult due to insufficient amount of sticking by the lancet L. The setting of dimension S can be performed by referring to the reference line 18a and the scales 18b shown in FIG. 1, which is convenient.

Figure 10:
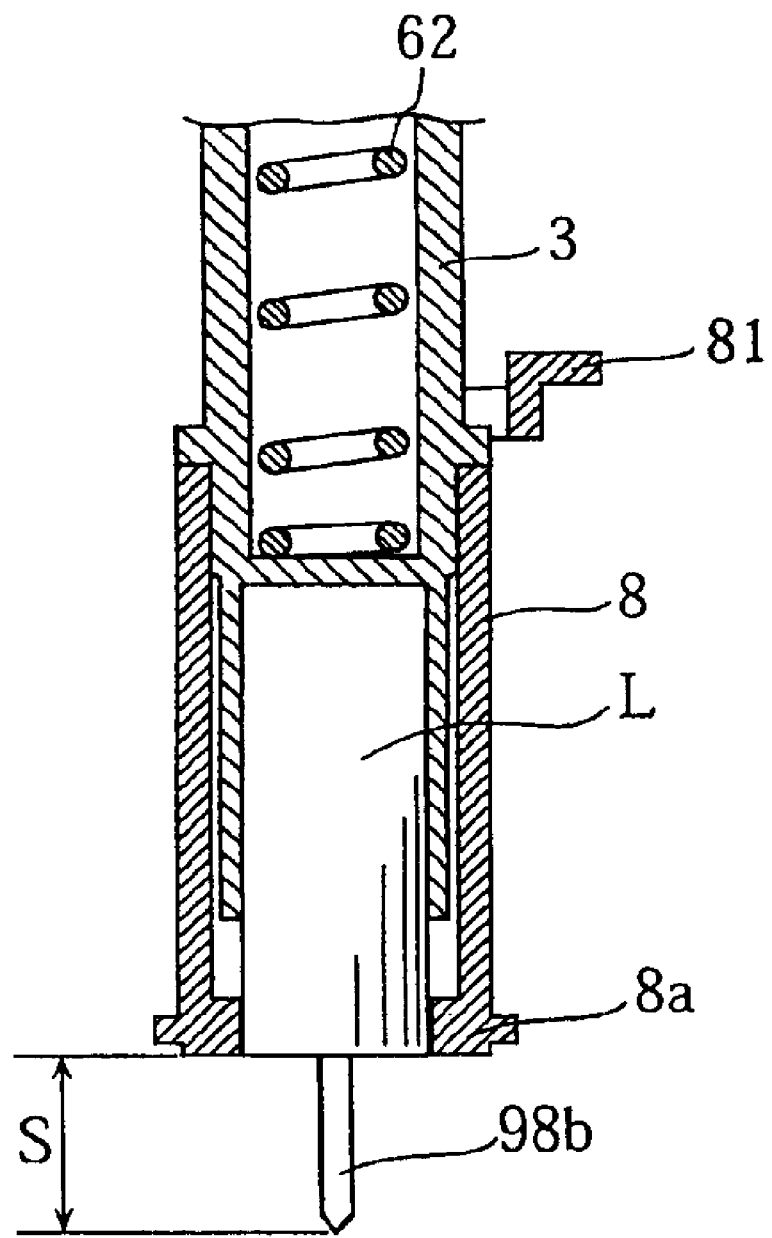
FIG. 10 is a sectional view of a principal portion in a state where the projecting amount of the lancet from the tip end portion of the auxiliary member is made large.

In this embodiment, the opening diameter at the tip end portion of the auxiliary member 8 is made larger than the main body 98a of the lancet L. Therefore, as shown in FIG. 10, the needle 98b of the lancet L can project entirely from the tip end portion 8a of the auxiliary member 8. Contrarily to this, the projecting amount S can be made close to zero. Thus, the sticking amount can be adjusted within a wide range, which provides further convenience. After the lancet L sticks into the skin 99, the lancet holder 3 can be retreated by an appropriate amount by utilizing the resilient force of the spring 65.

Figure 11:
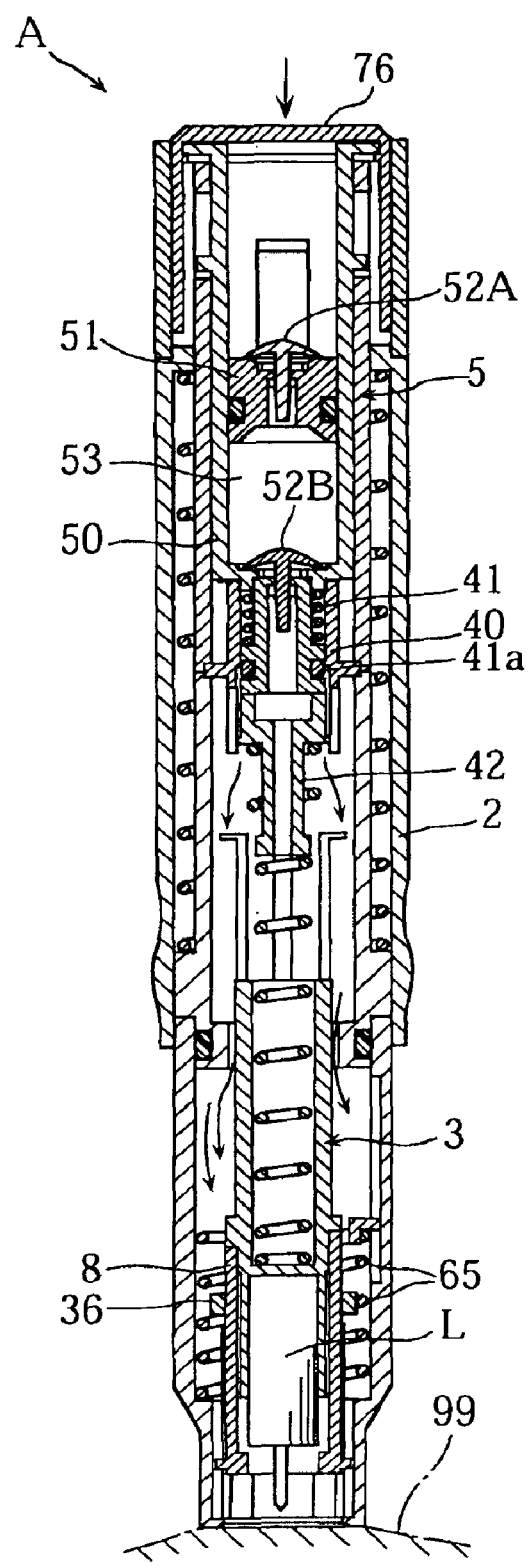
FIG. 11 is a sectional view illustrating the operation in eliminating negative pressure.

When the head cap 76 is further depressed as shown in FIG. 11, the O-ring 41a moves down to a position after passing through the portion of the sleeve 40 having the diameter D2. As a result, the communication path extending from the tip end portion of the housing 1 to the intake vent 55 of the cylinder 50 is released from the airtight state, so that the interior of the tip end portion of the housing 1 returns to atmospheric pressure. Therefore, the housing 1 can be easily removed from the skin 99.

The elimination of negative pressure described above can be performed only after the lancet L is stuck into the skin 99. Therefore, negative pressure acting on the skin 99 is prevented from erroneously being eliminated before the lancet L is stuck. Therefore, it is possible to reliably perform sticking of the lancet L into the skin 99 while bulging the skin 99 by negative pressure and promoting blood circulation at that portion. Both of the sticking of the lancet L and the eliminating of negative pressure can be easily performed by pushing down the head cap 76.

In the above-described example of usage of the lancing device A, the lancet L is stuck into the skin after negative pressure is produced in the tip end portion of the housing 1. However, such process steps in using the lancing device A may be performed in the reverse order. Specifically, the lancet L may first be stuck into the skin by depressing the head cap 65 and then negative pressure may be exerted on the portion stuck by the lancet L by reciprocating the outer cylinder 2. Also with this order of process steps, negative pressure promotes bleeding from the portion stuck by the lancet L. In this way, the lancing device A is conveniently used because the user can appropriately select to produce negative pressure before sticking the lancet L into the skin or after sticking the lancet into the skin.

FIGS. 13A, 13B, 14 and 15 illustrate another embodiment of the present invention. In these drawings, elements which are identical of similar to those of the above-described embodiment are designated by the same reference signs as those used in the above-described embodiment.

Figure 13A:
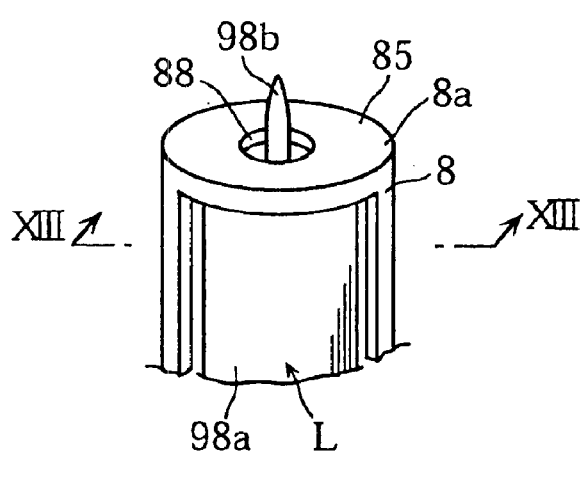
FIG. 13A is a perspective view illustrating a principal portion of another embodiment of auxiliary member.
Figure 13B:
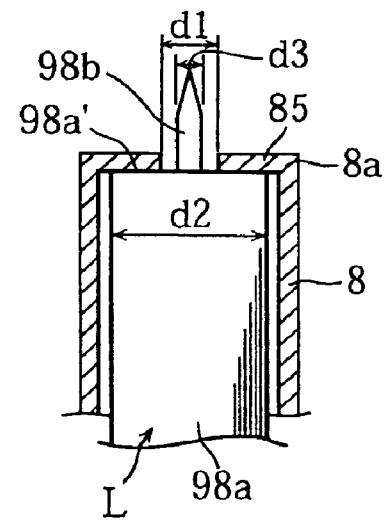
FIG. 13B is a sectional view taken along lines XIII—XIII in FIG. 13A.

In the structure shown in FIGS. 13A and 13B the tip end portion 8a of the auxiliary member 8 is formed with a patch plate portion 85. The patch plate portion 85 is generally circular and arranged in facing relationship to a tip end surface 98a' of the main body 98a of the lancet L. The patch plate portion 85 is formed with a hole 88 of a small diameter for passing the needle 98b of the lancet L.

With this structure, the diameter d1 of the hole 88 is made smaller than the diameter d2 of the main body 98a of the lancet L and hence closer to the diameter d3 of the needle 98b. Therefore, the auxiliary member 8 can set the sticking amount of the needle 98b into the skin more precisely.

Figure 14:
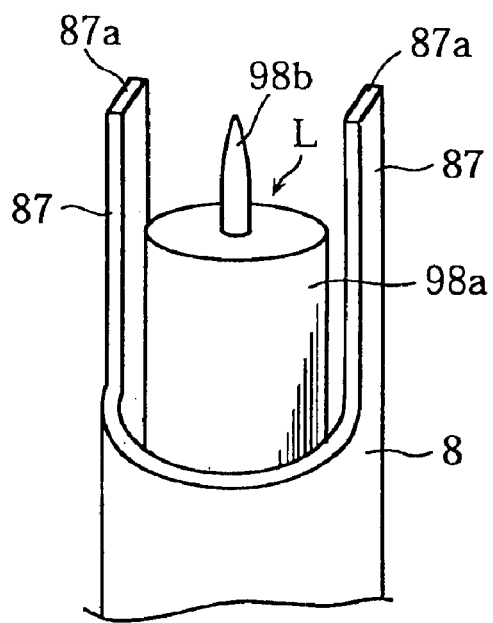
FIG. 14 is a perspective view illustrating a principal portion of another embodiment of auxiliary member.

In the structure shown in FIG. 14, the auxiliary member 8 includes two projections 87. The two projections 87 have respective end portions located on the sides of the needle 98b of the lancet L for sandwiching the needle 98b. In this case, when the needle 98b of the lancet L is stuck into the user's skin, an end surface 87a of each projection 87 comes into contact with the skin to prevent the needle 98b from sticking into the skin more than necessary. Thus, also in this case, the object of the present invention is attained. To precisely set the sticking amount of the lancet into the skin, it is preferable that the auxiliary member surrounds the entire circumference of the tip end portion of the lancet, but the present invention is not limited thereto.

Figure 15:
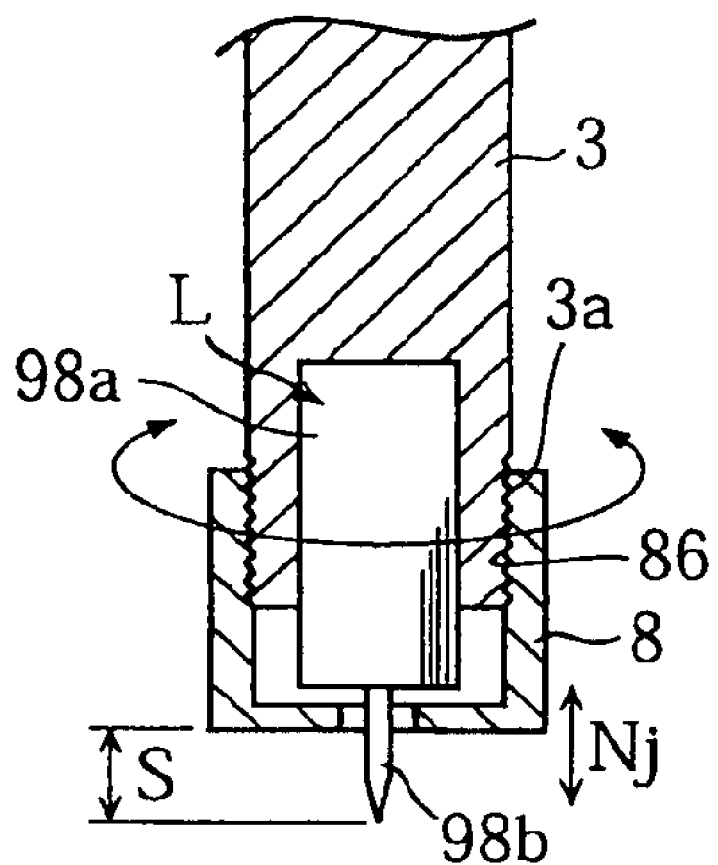
FIG. 15 is a sectional view illustrating a principal portion of another embodiment of auxiliary member mounting structure.
Figure 17:
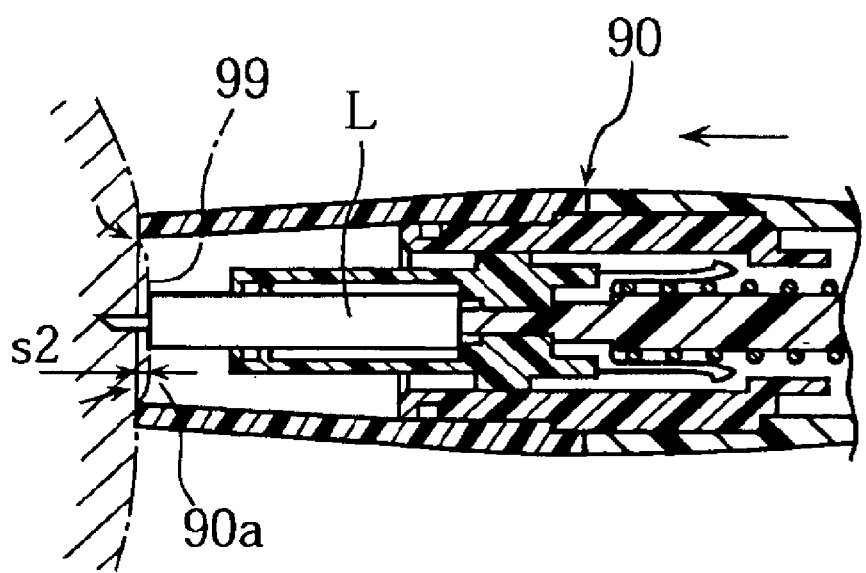
FIG. 17 is a sectional view of a principal portion of the prior art device for illustrating the operation.

In the structure shown in FIG. 15, the lancet holder 3 is provided with a male thread 3a formed around the tip end portion thereof, whereas the auxiliary member 8 is provided with a female thread 86. The auxiliary member 8 is directly attached to the lancet holder 3 by threading engagement of the thread portions 3a and 86. In such a structure, when the auxiliary member 8 is rotated, the auxiliary member 8 moves relative to the lancet holder 3 in the arrow Nj direction by the operation of the threads 3a and 86. Therefore, also with this structure, it is possible to vary the projecting amount of the tip end portion of the lancet L from the tip end portion of the auxiliary member 8, so that the object of the present invention is attained. In this way, in the present invention, the auxiliary member may be directly mounted to the lancet holder. In such a case, the mounting structure can be made simpler than the case where the auxiliary member is held by a member other than the lancet holder.

The lancing device according to the present invention is not limited to the above-described embodiments, and the specific structure of each part may be modified in various ways.

For example, in the present invention, the lancet may be advanced by a certain operation mechanism without using the lancet holder removably holding the lancet. Further, in the present invention, a needle may be attached to an appropriate member reciprocally arranged in the housing for serving as a lancet. Although it is preferable the lancet after use can be easily replaced with a new one, such a structure is not essential.

To make the auxiliary member movable relative to the lancet, means other than that of the above-described embodiment may be utilized. The lancing device according to the present invention may not be provided with a pump mechanism for producing negative pressure in the tip end portion of the housing. The operation mechanism in the present invention may be any mechanism if only it can advance the lancet from within the housing toward the opening of the housing.

What is claimed is:

1. A lancing device comprising:
   a housing having a tip end formed with an opening;
   a lancet arranged in the housing, the lancet including a main body and a lancing projection protruding forwardly from the main body, the lancing projection having a tip end;
   an operation mechanism for advancing the lancet within the housing toward the opening; and
   an auxiliary member for advancing together with the lancet toward the opening, the auxiliary member having a tip end portion that extends beyond the main body of the lancet toward the opening but is located short of the tip end of the lancing projection;
   the auxiliary member being capable of varying a position relative to the lancet for varying a projecting dimension of the lancing projection of the lancet from the tip end portion of the auxiliary member.

2. The lancing device according to claim 1, wherein the housing includes a sleeve rotatable relative to another portion of the housing;
   the variation of the position of the auxiliary member relative to the lancet being performed by rotating the sleeve.

3. The lancing device according to claim 2, further comprising a cam mechanism which moves the auxiliary member in a back-and-forth direction of the lancet when the auxiliary member is rotated relative to the lancet;

the auxiliary member engaging the sleeve to rotate relative to the lancet by rotating the sleeve.

4. The lancing device according to claim 1, further comprising a lancet holder for removably holding the lancet; the advancing movement of the lancet being performed by moving the lancet holder by an operation of the operation mechanism.

5. The lancing device according to claim 4, wherein the auxiliary member is attached to the lancet holder.

6. The lancing device according to claim 5, wherein the auxiliary member and the lancet holder are attached together by threading engagement, the variation of the position of the auxiliary member relative to the lancet being performed by rotating the auxiliary member and the lancet holder relative to each other.

7. The lancing device according to claim 1, wherein the tip end portion of the auxiliary member surrounds an entire circumference of the tip end portion of the lancet.

8. The lancing device according to claim 7, wherein the lancing projection comprises a needle projecting from a tip end surface of the main body; the tip end portion of the auxiliary member being provided with a patch plate portion facing the tip end surface of the main body, the patch plate portion being formed with a hole for passing the needle.

9. The lancing device according to claim 1, wherein the auxiliary member has a configuration capable of allowing the needle of the lancet to project from the tip end portion of the auxiliary member entirely throughout the length.

10. The lancing device according to claim 4, wherein the operation mechanism comprises:
a resilient member for biasing the lancet holder in the housing toward the opening;
a latch member for latching the lancet holder in the housing against resilient force of the resilient member;
an operation member exposed to an outside of the housing at least partially; and
a latch release member which operates to release the lancet holder from the latched state when the operation member is operated.

11. The lancing device according to claim 1, further comprising a pump mechanism;
the pump mechanism comprising:
a cylinder and a plunger defining a pressure chamber capable of communicating with an outside of the housing through an exhaust vent and capable of communicating with an inside of the tip end portion of the housing through an intake vent;
a plunger operation mechanism for reciprocally moving the plunger relative to the cylinder by an operation different from the operation of the operation mechanism;
a first non-return valve for opening or closing the exhaust vent, the first non-return valve keeping the exhaust vent open when the plunger reduces a volume of the pressure chamber; and
a second non-return valve for opening or closing the intake vent, the second non-return valve keeping the intake vent open when the plunger increases the volume of the pressure chamber.

12. The lancing device according to claim 11, wherein the plunger operation mechanism comprises an outer cylinder arranged outwardly on the housing for reciprocal movement, and connecting means for connecting the plunger to the outer cylinder so that the plunger moves reciprocally relative to the cylinder when the outer cylinder moves reciprocally.

13. A lancing device comprising:
a housing having a tip end formed with an opening;
a lancet arranged in the housing and having a tip end portion;
an operation mechanism for advancing the lancet within the housing toward the opening; and
an auxiliary member for advancing together with the lancet toward the opening, the auxiliary member having a tip end portion located for direct contact with a portion of skin drawn into the housing through the opening;
the auxiliary member being capable of varying a position relative to the lancet for varying a projecting dimension of the tip end portion of the lancet from the tip end portion of the auxiliary member.

14. A lancing device comprising:
a housing having a tip end formed with an opening;
a lancet arranged in the housing;
an operation mechanism for advancing the lancet within the housing toward the opening; and
an auxiliary member for advancing together with the lancet toward the opening, the auxiliary member having a tip end portion located on a side of a tip end portion of the lancet;
the auxiliary member being capable of varying a position relative to the lancet for varying a projecting dimension of the tip end portion of the lancet from the tip end portion of the auxiliary member;
wherein the housing includes a sleeve rotatable relative to another portion of the housing;
rotation of the sleeve causes the auxiliary member to move relative to the sleeve axially thereof for varying the position of the auxiliary member relative to the lancet.

15. The lancing device according to claim 14, further comprising a cam mechanism which moves the auxiliary member in a back-and-forth direction of the lancet when the auxiliary member is rotated relative to the lancet;
the auxiliary member engaging the sleeve to rotate relative to the lancet by rotating the sleeve.

16. A lancing device comprising:
a housing having a tip end formed with an opening;
a lancet arranged in the housing;
an operation mechanism for advancing the lancet within the housing toward the opening;
an auxiliary member for advancing together with the lancet toward the opening, the auxiliary member having a tip end portion located on a side of a tip end portion of the lancet; and
a pump mechanism;
the auxiliary member being capable of varying a position relative to the lancet for varying a projecting dimension of the tip end portion of the lancet from the tip end portion of the auxiliary member;
wherein the pump mechanism comprises:
a cylinder and a plunger defining a pressure chamber capable of communicating with an outside of the housing through an exhaust vent and capable of communicating with an inside of the tip end portion of the housing through an intake vent;
a plunger operation mechanism for reciprocally moving the plunger relative to the cylinder by an operation different from the operation of the operation mechanism;

a first non-return valve for opening or closing the exhaust vent, the first non-return valve keeping the exhaust vent open when the plunger reduces a volume of the pressure chamber; and a second non-return valve for opening or closing the intake vent, the second non-return valve keeping the intake vent open when the plunger increases the volume of the pressure chamber.

17. The lancing device according to claim 16, wherein the plunger operation mechanism comprises an outer cylinder arranged outwardly on the housing for reciprocal movement, and connecting means for connecting the plunger to the outer cylinder so that the plunger moves reciprocally relative to the cylinder when the outer cylinder moves reciprocally.

18. A lancing device comprising:

a housing having a tip end formed with an opening;

a lancet arranged in the housing;

an operation mechanism for advancing the lancet within the housing toward the opening;

an outer cylinder fitted around the housing for axial reciprocal movement; and an auxiliary member for advancing together with the lancet toward the opening, the auxiliary member having a tip end portion located on a side of a tip end portion of the lancet;

the auxiliary member being capable of varying a position relative to the lancet for varying a projecting dimension of the tip end portion of the lancet from the tip end portion of the auxiliary member;

the axial reciprocal movement of the outer cylinder causing air inside the housing to be pumped out of the housing.

* * * * *